United States Patent
De Bruijn et al.

(10) Patent No.: US 12,344,836 B2
(45) Date of Patent: Jul. 1, 2025

(54) TREATMENT OF PARASITIC INFECTIONS OF FISH SURFACES

(71) Applicants: Nederlands Instituut voor Ecologie (Nioo-Knaw), Wageningen (NL); University of Copenhagen, Copenhagen (DK)

(72) Inventors: Irene De Bruijn, Wageningen (NL); Josephus Maria Raaijmakers, Wageningen (NL); Kurt Buchman, Copenhagen (DK)

(73) Assignees: Nederlands Instituut voor Ecologie (Nioo-Knaw), Wageningen (NL); University of Copenhagen, Copenhagen (DK)

( * ) Notice: Subject to any disclaimer, the term of this patent is extended or adjusted under 35 U.S.C. 154(b) by 547 days.

(21) Appl. No.: 17/951,560

(22) Filed: Sep. 23, 2022

(65) Prior Publication Data

US 2023/0107426 A1    Apr. 6, 2023

Related U.S. Application Data

(62) Division of application No. 16/764,437, filed as application No. PCT/EP2018/081923 on Nov. 20, 2018, now abandoned.

(30) Foreign Application Priority Data

Nov. 21, 2017    (EP) .................................... 17202669

(51) Int. Cl.
| | |
|---|---|
| C12N 1/20 | (2006.01) |
| A61K 38/08 | (2019.01) |
| A61K 38/12 | (2006.01) |
| A61P 33/02 | (2006.01) |
| C12R 1/39 | (2006.01) |

(52) U.S. Cl.
CPC .............. *C12N 1/205* (2021.05); *A61K 38/08* (2013.01); *A61K 38/12* (2013.01); *A61P 33/02* (2018.01); *C12R 2001/39* (2021.05)

(58) Field of Classification Search
CPC ........ C12N 1/205; A61K 38/08; A61K 38/12; A61P 33/02
See application file for complete search history.

(56) References Cited

FOREIGN PATENT DOCUMENTS

DE    10328003 A1    8/2004

OTHER PUBLICATIONS

Kuiper, Irene et al. "Characterization of two Pseudomonas putida lipopeptide biosurfactants, putisolvin I and II, which inhibit biofilm formation and break down existing biofilms." Molecular microbiology vol. 51,1 (2004): 97-113. doi:10.1046/j.1365-2958.2003.03751.x.

Verbruggen, Bas et al. "Molecular Mechanisms of White Spot Syndrome Virus Infection and Perspectives on Treatments." Viruses, vol. 8, No. 23, 2016, pp. 1-29, doi:10.3390/v8010023.

M. Monica et al. "The efficacy of Poly-b-Hydroxy Butyrate (PHB)/biosurfactant derived from *Staphylococcus hominis* against White Spot Syndrome Virus (WSSV) in Penaeus mondon." Fish and Shellfish Immunology, vol. 71, 2017, pp. 399-410.

Donio, Mariathason Birdilla Selva et al. "*Halomonas* sp. BS4, A biosurfactant producing halophilic bacterium isolated from solar salt works in India and their biomedical importance." SpringerPlus, vol. 2, No. 149, 2013, pp. 2-10.

Donio, MBS et al. "Isolation and characterization of halophilic *Bacillus* sp. BS3 able to produce pharmacologically important biosurfactants." Asian Pacific Journal of Tropical Medicine, 2013, pp. 876-883.

Liu, Yiying, et al. "Diversity of Aquatic *Pseudomonas* Species and Their Activity against the Fish Pathogenic Oomycete Saprolegnia." PLoS ONE, vol. 10, No. 8, 2015, e0136241. doi:10.1371/journal.pone/0136241.

Aihua, L. and Buchmann, K. "Temperature- and salinity-dependent development of a Nordic strain of Ichtyophthirius multifiliis from rainbow trout." Journal of Applied Ichthyology, 17, 2001, pp. 273-276.

De Brujin, I. et al. "Massetolide A Biosnythesis in Pseudomonas fluorescens." American Society for Microbiology, vol. 190, No. 8, 2008, pp. 2777-2789.

De Brujin, I. et al. "Genome-based discovery, structure prediction and functional analysis of cyclic lipopeptide antibiotics in *Pseudomonas* species." Molecular Microbiology, vol. 63, No. 2, 2007, pp. 417-428.

Kruijt, M. et al. "Functional, genetic and chemical characterization of biosurfactants produced by plant growth-promoting Pseudomonas putida 267." Journal of Applied Microbiology, vol. 107, 2009, pp. 546-556.

Liu, Y. et al. "Diversity of Aquatic *Pseudomonas* Species and Their Activity against the Fish Pathogenic Oomycete Saprolegnia." PLoS ONE 10(8): e0136241. doc.10.1371/journal.pone.0136241, 2015.

Xueqin, J. et al. "Comparative effects of four feed types on white spot disease susceptibility and skin immune parameters in rainbow trout, *Oncorhynchus mykiss* (Walbaum)." Journal of Fish Diseases, vol. 35, 2012, pp. 127-135.

International Search Report for International Application No. PCT/EP2018/081923, dated Jan. 18, 2019 (3 pages).

*Primary Examiner* — Sikarl A Witherspoon

(74) *Attorney, Agent, or Firm* — Occhiuti & Rohlicek LLP

(57) ABSTRACT

The invention relates to the use of bacterial lipopeptide biosurfactants in the treatment of white spot disease in fresh water and marine fish. Particularly useful for treatment of white spot disease are viscosin-like lipopeptide biosurfactants obtainable from the *Pseudomonas fluorescens* strain H6, massetolide or a derivative thereof and putisolvin or a derivative thereof.

20 Claims, 3 Drawing Sheets

TREATMENT OF PARASITIC INFECTIONS OF FISH SURFACES

CROSS-REFERENCE TO RELATED APPLICATIONS

This application is a divisional application of U.S. application Ser. No. 16/764,437, filed May 15, 2020, which is a national stage application under 35 U.S.C. 371 of International Application No. PCT/EP2018/081923 filed on Nov. 20, 2018, which claims priority to European Application No. 17202669.2 filed on Nov. 21, 2017, the contents of all of which are hereby incorporated by reference in their entireties.

FIELD OF THE INVENTION

The present invention relates to the treatment of parasitic infections causing white spot disease in fish.

BACKGROUND OF THE INVENTION

Diseases in fish, such as freshwater fish caused by parasites in and on their surfaces (gills, skin, fins) are an economic challenge in fish production industry targeting fish for consumption as well as ornamental fish. One important disease is white spot disease of freshwater fish in particular caused by the parasitic ciliate *Ichthyophthirius multifiliis* which leads to high morbidity and mortality in both wild and cultured fish, worldwide.

Several chemicals are currently being applied to control white spot disease in fish, such as in freshwater fish.

Following the ban of the organic dye malachite green, previously used for treatment of the disease, fish farmers apply a number of compounds for disease control including sodium percarbonate, copper sulphate, formalin, peracetic acid and totrazuril. These compounds, however, can have adverse environmental effects. Also plant extracts have attracted considerable attention due to their effect on certain life stages of the parasite and recently purified plant derived compounds comprising cynatratoside-C, sanguinarine, dihydrosanguinarine and dihydrochelerythrine, pentagalloylglucose have exhibited some antiparasitic effects in laboratory experiments. However, despite the promising reports on antiparasitic effects of natural, semi-synthetic and synthetic plant-derived products, questions on their residual and toxic effects on the environment, fish and humans remain unsolved.

White spot disease causes severe economic losses in fresh water and sea water aquaculture. Accordingly, there is a need for an effective and safe remedy against white spot disease in fish.

SUMMARY OF THE INVENTION

According to the present invention it was surprisingly found that lipopeptide surfactants can be used in the treatment of white spot disease in fish.

Accordingly, the present invention relates to the use of lipopeptide surfactants in the treatment of white spot disease in fish. The present invention relates in particular to the use of bacterial lipopeptide surfactants in the treatment of white spot disease.

Furthermore, such treatment is considered safe as fish showed no adverse immediate or late signs following several hours of incubation in the effective lipopeptide biosurfactant concentrations.

Accordingly surfactant lipopeptides may find application as an antiparasitic control agent in aquacultured fish.

To this end, the fish or fish tank water may be treated with the isolated surfactant lipopeptide, or with compositions or formulations containing this lipopeptide.

Alternatively, the fish may be treated with the bacterial isolate wherein the bacteria are capable to produce said lipopeptide biosurfactant.

DETAILED EMBODIMENTS OF THE INVENTION

The present invention relates to a lipopeptide biosurfactant for use in the treatment of white spot disease in fish, such as in fresh water fish and in marine fish.

Examples of parasites causing white spot disease in fish are parasites of the family termed Ichthyophthiriidae, and in particular *Ichthyophthirius multifiliis* causing freshwater white spot disease. A further example is the parasite *Cryptocaryon irritans* (originally classified as *Ichthyophthirius marinus*) causing marine white spot disease.

Accordingly, in a particular embodiment, the present invention relates to lipopeptide biosurfactant for use in the treatment of white spot disease, such as caused by *Ichthyophthirius multifiliis* infection and *Cryptocaryon irritans* infection.

More in particular, the present invention relates to lipopeptide biosurfactant for use in the prevention of white spot disease, such as caused by *Ichthyophthirius multifiliis* infection in fresh water fish and *Cryptocaryon irritans* in marine fish.

Herein, the term "fresh water fish" relates to fish living at least during a certain stage of its life cycle in fresh water. Suitable examples are fish raised for consumption in aquaculture (such as salmonids (exemplified by rainbow trout (*Oncorhynchus mykiss*)), cyprinids (exemplified by grass carp (*Ctenopharyngodon idella*), black carp (*Mylopharyngodon piceus*), silver carp (*Hypophthalmichthys molitrix*), common carp (*Cyprinus carpio*), bighead carp (*Hypophthalmichthys nobilis*), catla (Indian carp, *Catla catla*), crucian carp (*Carassias carassius*), roho *labeo* (*Labeo roltita*)), other fish families including tilapia (exemplified by nile tilapia (*Oreochromis niloticus*)), milkfish (*Chanos chanos*), catfish (exemplified by Amur catfish (*Silurus asotus*)), Wuchang bream (*Megalobrama amblycephala*), northern snakehead (*Channa argus*) as well as a long range of ornamental fish species maintained in aquaria.

As referred herein, "marine fish" relates to fish species living at least a part of their life in marine waters. Examples are fish raised for aquaculture in mariculture systems such as gilthead seabream (*Sparus auratus*) and seabass (*Dicentrarchus labrax*). In addition, a long range ornamental fish species used in marine aquaria is covered by the term.

As referred herein the expression "lipopeptide biosurfactant" relates to a molecule consisting of a lipid connected to a peptide, generally a cyclic peptide, with surfactant properties (i.e. lowering surface tension of fluids). Lipopeptide biosurfactants can be produced by bacteria. Generally, the biosynthetic pathway encoding the lipopeptide surfactant within a given bacterial strain leads to a single main lipopeptide surfactant and minor amounts of structurally related derivatives of the main lipopeptide surfactant.

Known bacterial lipopeptide biosurfactants are for example surfactin and derivatives thereof, daptomycin and derivatives thereof, massetolide and derivatives thereof, viscosin and derivatives thereof, thanamycin and derivatives thereof and putisolvin and derivatives thereof.

Suitable massetolide lipopeptide surfactants for use according to the present invention are massetolide A, massetolide B, massetolide C, massetolide D, massetolide E, massetolide F, massetolide G and massetolide H.

Treatment of white spot disease in fish in particular comprises the prevention of white spot disease by preventing the development of the tomonts and tomocysts and more in particular by preventing the development of the free-living theronts of the organisms causing white spot disease in fish, like *Ichthyophthirius multifiliis* and *Cryptocaryon irritans*.

A further viscosin-like lipopeptide biosurfactant obtainable from the bacterium *Pseudomonas fluorescens* strain H6 was recently reported to kill zoospores of the oomycete fish pathogen *Saprolegnia diclina* (de Bruijn et al. 2007; Liu et al. 2015) and thus might be useful to control *Saprolegnia* infections.

Surprisingly, we discovered that this vicosin-like lipopeptide biosurfactant of *Pseudomonas fluorescens* strain H6 can also suitably be used for the treatment of white spot disease in fish such as infections caused by *Ichthyophthirius multifiliis*.

In a particular embodiment, the present invention relates to a bacterial lipopeptide biosurfactant obtainable from the *Pseudomonas fluorescens* strain H6 or a derivative thereof for use in the treatment of *Ichthyophthirius multifiliis* infection in fish.

In a further embodiment, the present invention relates to a composition comprising at least one lipopeptide biosurfactant for use in the treatment of white spot in fish, in particular in fresh water fish and in marine fish.

In a further embodiment, the present invention relates to a composition comprising at least one lipopeptide biosurfactant for use in the treatment of *Ichthyophthirius multifiliis* infection in fish, in particular in fresh water fish.

In a further embodiment, the present invention relates to a composition comprising a bacterial lipopeptide biosurfactant obtainable from the *Pseudomonas fluorescens* strain H6 for use in the treatment white spot in fish, in particular in fresh water fish and in marine fish.

In a further embodiment, the present invention relates to a composition comprising a bacterial lipopeptide biosurfactant obtainable from the *Pseudomonas fluorescens* strain H6 or a derivative thereof for use in the treatment of *Ichthyophthirius multifiliis* infection in fish, in particular in fresh water fish.

A composition suitable according to the present invention may predominantly comprise the lipopeptide or lipopeptides, for example the one or more lipopeptides together with one or more carriers, or may for example comprise a slow-release form (i.e. granules) which sheds the lipopeptide biosurfactant(s) over a prolonged period.

In a particular embodiment, the composition suitable according to the present invention may be prepared from a freeze-dried solution of the lipopeptide or lipopeptides by dissolving the freeze-dried solution in water, such as sterile distilled water.

Alternatively, the lipopeptide biosurfactant may be administered to the fish as a bacterial culture, which is capable to produce the lipopeptide in aquaculture.

Accordingly, in a further embodiment, the invention relates to a bacterial isolate wherein the bacteria are capable to produce lipopeptide surfactant for use in the treatment white spot in fish, in particular fresh water fish and marine fish.

In a further embodiment, the invention relates to a bacterial isolate wherein the bacteria are capable to produce lipopeptide surfactant for use in the treatment of *Ichthyophthirius multifiliis* infection in fish, in particular fresh water fish.

In a further embodiment, the invention relates to a bacterial isolate of the *Pseudomonas fluorescens* strain H6 for use in the treatment of white spot in fish, in particular in fresh water fish and in marine fish.

In a further embodiment, the invention relates to a bacterial isolate wherein the bacteria are capable to produce a massetolide and/or derivatives for use in the treatment of white spot disease in fish, in particular in fresh water fish.

In a further embodiment, the invention relates to a bacterial isolate wherein the bacteria are capable to produce a putisolvin and/or derivatives for use in the treatment of white spot disease in fish, in particular in fresh water fish.

In a further embodiment, the invention relates to a bacterial isolate of the *Pseudomonas fluorescens* strain H6 or a derivative thereof or a derivative thereof for use in the treatment of *Ichthyophthirius multifiliis* infection in fish.

A sample of the *Pseudomonas fluorescens* strain H6 has been deposited on Nov. 1, 2017 under the Regulations of the Budapest Treaty in the CBS collection of the Westerdijk Fungal Biodiversity Institute with deposit number CBS 143505.

The isolation and characterization of the lipopeptide biosurfactant of *Pseudomonas fluorescens* strain H6 has been described by Liu et al. (2015). This viscosin-like lipopeptide biosurfactant was found to be clearly distinguished from the well-known lipopeptide biosurfactants of related strains such as the massetolide lipopeptide which can be obtained from *Pseudomonas fluorescens* SS101, the viscosin lipopeptide which can be obtained from *Pseudomonas fluorescens* SBW25 and the putisolvin lipopeptide which can be obtained from Pseudomons *putida* 267.

It was shown that these lipopeptide biosurfactants have a strong in vitro antiparasitic effect on the fish pathogenic ciliate *Ichthyophthirius multifiliis*. *Ichthyophthirius multifiliis* is a pathogenic ciliate with different life cycle stages, the infective theront stage, the trophont stage in the fish epidermis, the tomont (the stage attained in the water after the trophont has left the fish skin), the tomocyst containing tomites which are released to the water as theronts. The life cycle stages including tomonts, tomocysts and theronts were found susceptible to the H6 lipopeptide biosurfactant. Theronts were the most sensitive showing 100% mortality within 30 min in as low concentrations as 10 and 13 µg/ml. Tomonts were the most resistant but were killed still fast at the higher concentrations of 100 and 1000 µg/ml. Tomocysts are generally resistant to chemical and medical treatment due to the surrounding protective cyst wall. Surprisingly, they were sensitive to the lipopeptide biosurfactant from *Pseudomonas fluorescens* strain H6. The lipopeptide biosurfactant, even at low concentrations of 10 and 13 µg/ml, (penetrated the cyst wall and) killed the enclosed tomites within a few minutes.

Accordingly, this lipopeptide biosurfactant of *Pseudomonas fluorescens* strain H6 may find further application as an antiparasitic control agent in aquacultured fish, in particular in aquacultured trout, such as in rainbow trout.

As mentioned above, the present invention also relates to the use of other lipopeptide biosurfactants for the control of white spot disease. It has been shown for example that also massetolide and putisolvin show a pronounced in vitro activity against various developmental stages of the parasite causing white spot disease in fish.

Accordingly, in a particular embodiment, the present invention relates to the use of a lipopeptide biosurfactant selected from (a) a viscosin-like lipopeptide (such as lipopeptide biosurfactant obtainable from the *Pseudomonas fluorescens* strain H6) or a derivative thereof, (b) a massetolide (such as a massetolide surfactant obtainable from *Pseudomonas fluorescens* strain SS101) or a derivative thereof, and (c) a putisolvin (such as the putisolvin biosurfactant obtainable from *Pseudomonas putida* 267) or a derivative thereof in the treatment of white spot disease in fish, in particular in fresh water fish and in marine fish, and more particular in the treatment of white spot disease caused by the pathogenic ciliate *Ichthyophthirius multifiliis*.

In the applications mentioned above, the lipopeptide according to the present invention may be administered to the fish (such as to the fish tank water) in a concentration of 10-1000 µg/ml, such as 10-100 µg/ml of the lipopeptide biosurfactant.

Accordingly, in a particular embodiment, the present invention relates to the use of a lipopeptide biosurfactant selected from (a) a viscosin-like lipopeptide (such as lipopeptide biosurfactant obtainable from the *Pseudomonas fluorescens* strain H6) (b) a massetolide (such as a massetolide biosurfactant obtainable from *Pseudomonas fluorescens* strain SS101) or a derivative thereof, and (c) a putisolvin (such as the putisolvin biosurfactant obtainable from *Pseudomonas putida* 267) or a derivative thereof in a concentration of 10-1000 µg/ml, such as in a concentration of 10-100 µg/ml, in the treatment of white spot disease in fish, in particular in fresh water fish, and more particular in the treatment of white spot disease caused by the pathogenic ciliate *Ichthyophthirius multifiliis*.

The treatment may be a one-time treatment after infection has been identified. Alternatively the treatment may be performed several times, such as once a day or once a week.

Use of the verb "to comprise" and its conjugations does not exclude the presence of elements or steps other than those stated in a claim. Unless the context clearly requires otherwise, throughout the description and the claims, the words "comprise", "comprising", and the like are to be construed in an inclusive sense as opposed to an exclusive or exhaustive sense; that is to say, in the sense of "including, but not limited to".

The article "a" or "an" preceding an element does not exclude the presence of a plurality of such elements.

The terms "treatment" and "control" or "controlling" may be used interchangeably and may all relate to prevention and curing of diseases.

The various aspects discussed in this patent can be combined in order to provide additional advantages. Further, the person skilled in the art will understand that embodiments can be combined, and that also more than two embodiments can be combined. Furthermore, some of the features can form the basis for one or more divisional applications.

NOTIFICATION

The project leading to this patent application has received funding from the European Union's Horizon 2020 research and innovation programme under grant agreement No 634429.

EXAMPLES

Materials and Methods

Figure 1A:
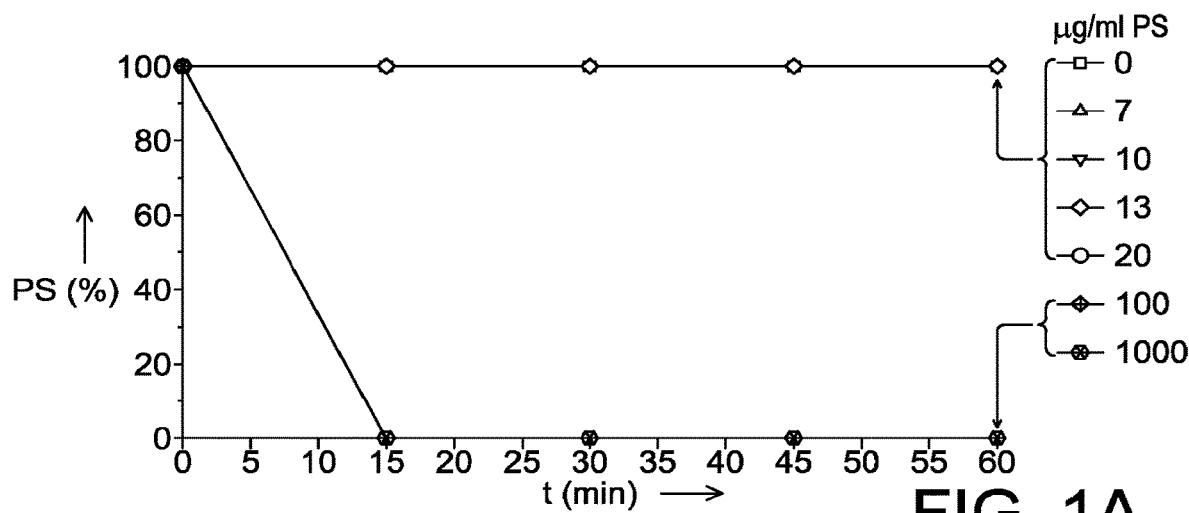
FIG. 1A is a graph showing effects of *Pseudomonas fluorescens* H6 lipopeptide biosurfactant (PS) on *Ichthyophthirius multifiliis* tomonts.

Parasites:

A Danish strain of *Ichthyophthirius multifiliis* was established in a laboratory population of rainbow trout originally raised in a disease free recirculation system (Xueqin et al. (2012)).

Parasites were collected from infected rainbow trout reared in a Danish commercial trout farm (Jutland, western part of Denmark) as previously described (Aihua & Buchmann, (2001)). Infected live fish were transported to the University of Copenhagen.

*Ichthyophthirius multifiliis* parasites were isolated at room temperature by placing fins and gills, recovered from a fish euthanized (300 mg/L of tricaine methanesulfonate, MS222, Sigma-Aldrich, Denmark), in Petridishes with freshwater (22° C.). This induced release of epidermal trophonts to leave the fish tissues as tomonts. Some were isolated and used directly for lipopeptide biosurfactant exposure studies. Others were incubated further and transformed into tomocysts each containing several hundreds of tomites (24 h). A subpopulation of these were used for exposure and others were incubated further untill they released theronts within 24-30 h. These were isolated and similarly used for in vitro evaluation of lipopeptide biosurfactant effects.

*Pseudomonas fluorescens* H6 lipopeptide biosurfactant (PS):

A lipopeptide biosurfactant of *Pseudomonas fluorescens* strain H6 was extracted according to the method described by Liu et al. (2015).

*Pseudomonas fluorescens* strain H6 was grown on *Pseudomonas* agar plates (20 ml plates) for 48 h at 25C. Cells of strain H6 were collected from the agar plates and suspended in sterile de-mineralized water (5-10 ml per plate), and vortexed to homogenize the cell suspension. Cell suspensions were then centrifuged twice for 10 min at 9,000 rpm (4C) and supernatant filter-sterilised with 0.2 µm filters. The lipopeptide biosurfactant present in the cell-free culture supernatant was precipitated by acidification of the supernatant with 9% (v/v) HCl to pH 2.0. Precipitation was allowed for 1 h on ice. The precipitate was collected by centrifugation at maximum speed and washed three consecutive times with acidified (pH 2.0) demineralized water. Demineralized water was added to the washed precipitate and the pH was adjusted to 8.0 with 0.2 M NaOH to allow the precipitate to dissolve. The resulting solution was freeze-dried.

A stock solution of 10 mg/mL was prepared by dissolving the product in sterile distilled water whereafter a dilution series was prepared for parasite exposures.

In Vitro Incubation and Exposure:

Glass plates (thickness 6 mm) each with 30 concave wells (diameter 25 mm, depth 3 mm, maximum water capacity 2000 µL) were used for incubation of parasite life stages (theronts, tomont and tomocysts).

The final concentrations of the lipopeptide biosurfactant in the wells were 1000, 100, 20, 13, 10, 7, 5, 2.5, 2 and 1 µg/mL and all concentrations were tested in triplicate for each parasite stage.

The number of parasites in each well was for theronts 20-25, for tomonts 2 and for tomocysts 2.

The volume added into each well was 100 µL composed by mixing 50 µL of lipopeptide biosurfactant solution with 50 µL of fresh water containing parasites.

The experiment was performed at room temperature (22° C.) and parasite motility was recorded at 0, 15, 30, 45, 75, 60 and 90 min. The experiments were conducted in triplicate.

Monitoring Effect of Lipopeptide Biosurfactant on Motility of Parasites:

A Leica M Z 95 dissection microscope (magnification 6-40x) was used for monitoring motility of tomonts, tomocysts and theronts.

Motility was recorded as presence of ciliary activity and cell movements of free theronts, free tomonts and tomites enclosed in tomocysts.

Non-motile and lysed tomites, theronts and tomonts were considered dead.

Sensitivity of Fish to Lipopeptide Biosurfactant:

Rainbow trout (2 x3) were exposed in plastic fish tanks (total volume 3 L), each containing 1 L of lipopeptide biosurfactant solution and three rainbow trout, to concentrations of lipopeptide biosurfactant (10 and 13 µg/mL) which were found effective for all tested parasite life stages within 90 min. Three control fish were kept under the same conditions but without lipopeptide biosurfactant.

Fish were monitored in the lipopeptide biosurfactant solution for 3 h after exposure whereafter they were transferred to 80 L tanks containing only pure water and observed for any adverse behavioural signs (balance disturbances, lethargia, anorexia) for 7 days.

Data Analysis

As no significant differences between the triplicate wells were observed with regard to parasite survival (three different parasite life stages in different lipopeptide biosurfactant concentrations), data from these were pooled.

Survival of the different parasite life stages was visualized in a Kaplan-Meier plot and statistically tested by Dunn's multiple comparison test with a probability level of 5%.

All the statistical analyses and graphs in this study were performed by using Graph Pad Prism Version 5.

Example 1

In vitro effects *Pseudomonas fluorescens* strain H6 lipopeptide biosurfactant on *Ichthyophthirius multifiliis*

Tomonts

*Ichthyophthirius multifiliis* tomonts were only sensitive to the two highest concentrations (1000 and 100 µg/mL PS), which killed all parasites within 15 min (FIG. 1A).

Figure 2:
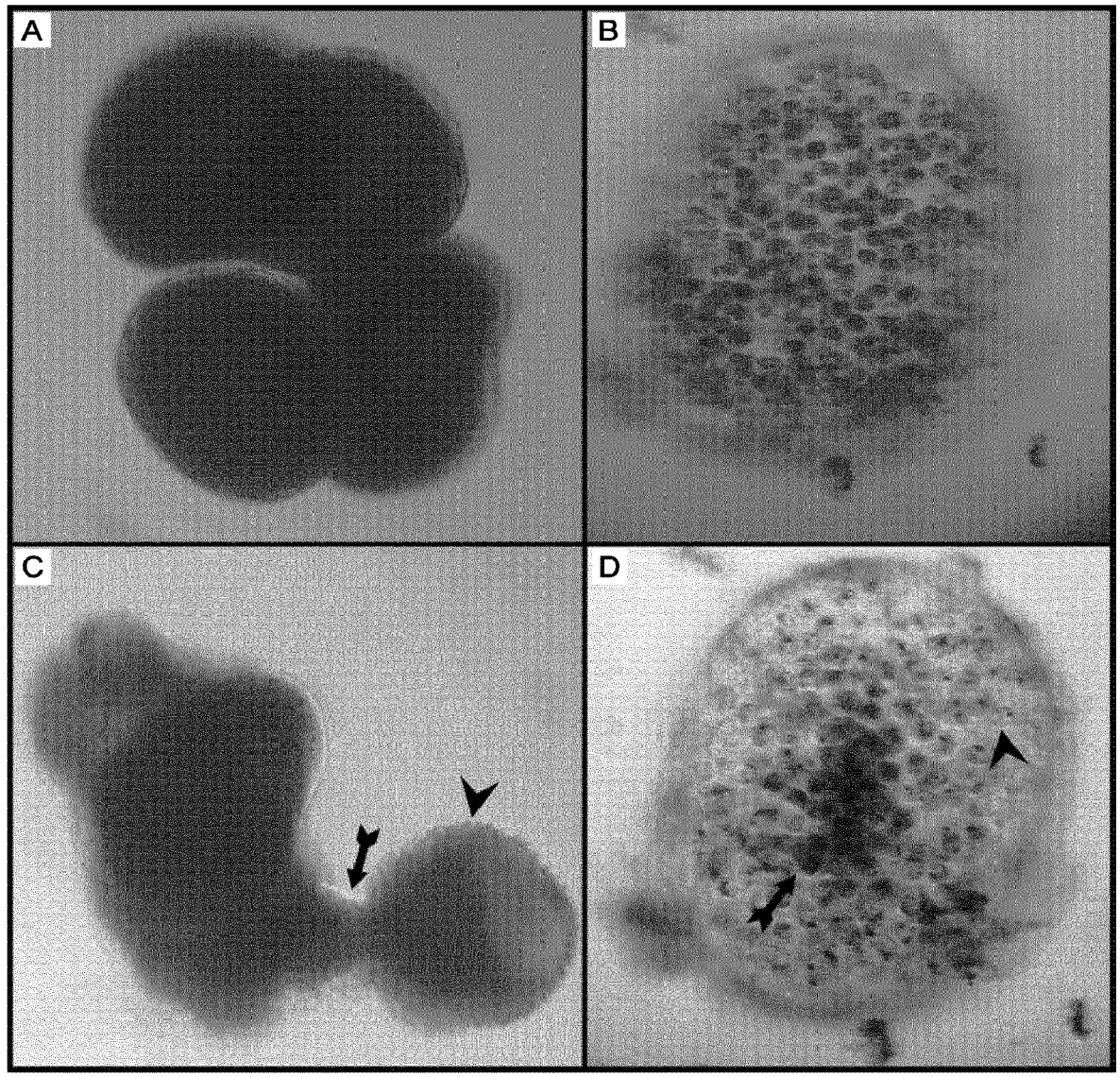
FIG. 2 are photos of tomonts released from the fish skin and tomocysts with enclosed tomites of *Ichthyophthirius multifiliis* affected by PS. A) Tomonts without PS. B) Tomocysts with enclosed tomites after 30 sec exposure to PS. C) Tomont showing a membrane disruption and release of cytoplasm following 15 min of PS exposure. D) Tomocyst with enclosed dead tomites in the cyst center after 15 min PS exposure.

Cytoplasmic movements inside the tomonts (FIG. 2A) initially increased when exposed to the lipopeptide biosorfactant, whereafter a disruption of the membrane followed and finally cytoplasm was released into the surroundings of the tomonts (FIG. 2C).

A 10 µg/mL PS concentration had no effect on this parasite life stage within the observation period tested.

Tomocysts

Figure 1B:
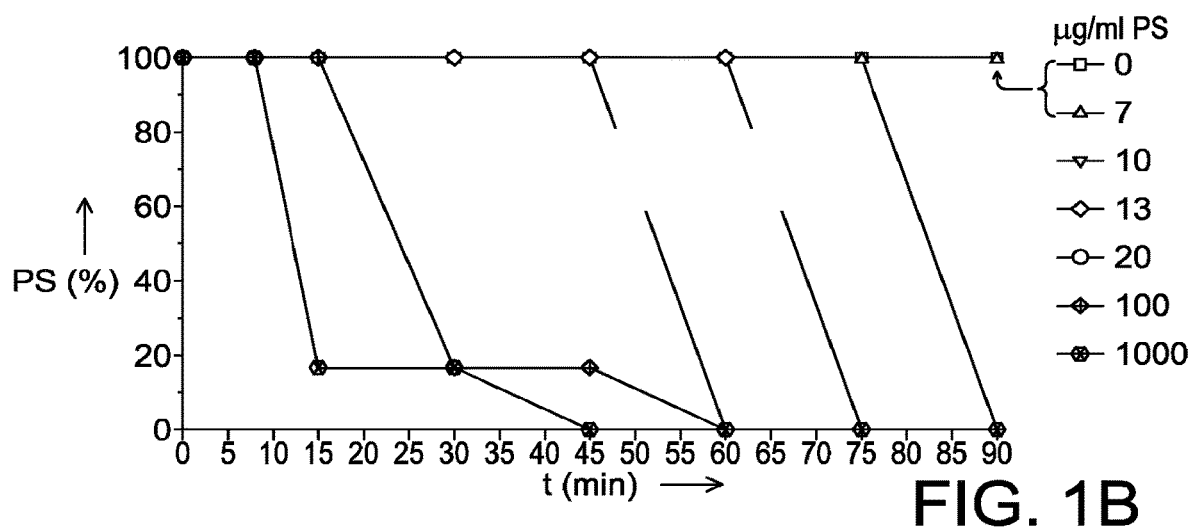
FIG. 1B is a graph showing the effects of *Pseudomonas fluorescens* H6 lipopeptide biosurfactant (PS) on *Ichthyophthirius multifiliis* tomocysts.

*Ichthyophthirius multifiliis* tomocysts, with their enclosed tomites (FIG. 2B), showed a different sensitivity to the lipopeptide biosurfactant when compared to tomonts (FIG. 1B).

At the highest tested concentration of 1000 µg/mL PS, the majority of tomites in the tomocysts (83%) were immotile after 15 min of exposure (FIG. 1B). When exposed to 100 µg/mL PS, immobilization was observed for 83% tomites after 30 min. After 60 min, all tomocysts with their content of tomites were dead (FIG. 2D).

Dead tomites were concentrated at the center of the tomocyte because tomites in the tomocyst moved away from the periphery immediately after PS addition (FIG. 2D).

The effect of 13 and 10 µg/mL PS was slightly lower; nevertheless, all parasites were killed within 75 min and 90 min, respectively.

Tomocysts were phenotypically not affected at PS concentrations of 0 and 7 µg/mL.

Theronts

Figure 1C:
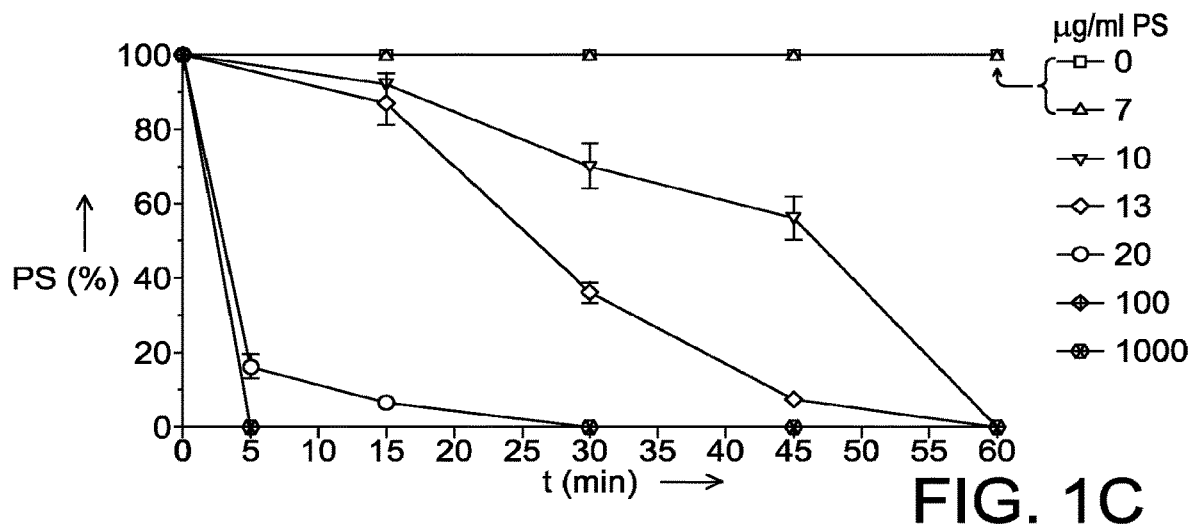
FIG. 1C is a graph showing the effects of *Pseudomonas fluorescens* H6 lipopeptide biosurfactant (PS) on *Ichthyophthirius multifiliis* theronts.

*Ichthyophthirius multifiliis* theronts showed a high sensitivity towards PS and when exposed to 1000 and 100 µg/mL PS theronts showed 100% mortality within 5 min (FIG. 1C). In 20 µg/mL PS, less than 20% survival was seen at this time point and the remaining theronts were killed after 30 min.

Concentrations of 13 and 10 µg/mL PS were lethal for theronts within 60 min. Concentrations of 7 µg/mL PS and lower had no visual effect even after 90 min.

Example 2

Sensitivity of Fish to *Pseudomonas* Lipopeptide Biosurfactant

Rainbow trout showed no immediate or late adverse reactions when exposed for 3 h to PS concentrations of 10 and 13 µg/mL. No toxic effects on fish could be detected.

Example 3

Figure 3:
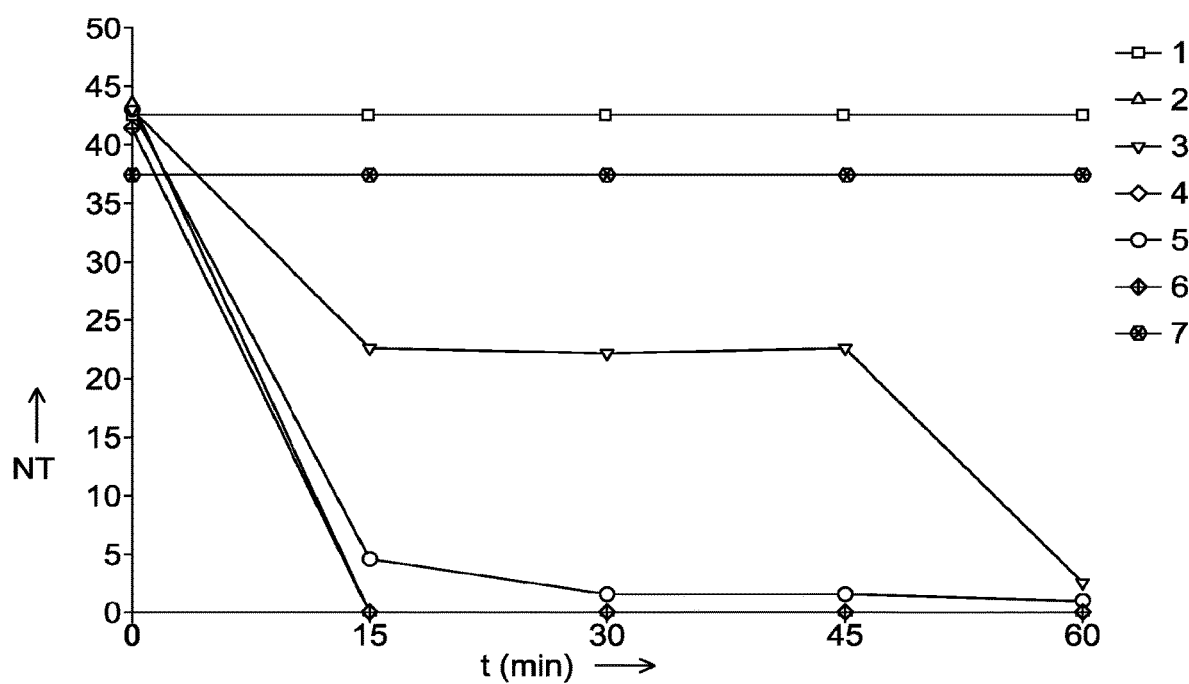
FIG. 3 is a graph showing the effect of biosurfactants on number of theronts. The biosurfactants tested were massetolide obtained from *Pseudomonas fluorescens* SS101, the putisolvin-like biosurfactant from *Pseudomonas putida* 267 and the viscosin-like biosurfactant of *Pseudomonas* H6. In this figure the following data are included (1) water control; (2) 0.15 mg/ml viscosin (H6); (3) 0.015 mg/ml viscosin (H6); (4) 0.15 mg/ml massetolide (SS101); (5) 0,015 mg/ml massetolide (SS101); (6) 0.15 mg/ml putisolvin (267); (7) 0,015 mg/ml putisolvin (267).

Comparison of in vitro activity of various biosurfactants against tomonts and theronts Collection of *I. multifillis* was performed as described above. Extracts of the biosurfactant massetolide A was obtained from *Pseudomonas fluorescens* SS101 as described in De Bruijn et al (2008), the putisolvin-like biosurfactant from *Pseudomonas putida* 267 as described in Kruijt et al (2008) and the viscosin-like biosurfactant of *Pseudomonas* H6 as described above. A stock solution of 15 mg/mL was prepared for each surfactant by dissolving the product in sterile distilled water whereafter a dilution series was prepared for parasite exposures that was performed as described in above. Concentrations of 0.15 and 0.015 mg/ml were tested for all three biosurfactants against tomonts (one replicate) and theronts (in duplicate) and mortality recorded every 15 min up to 1 h of exposure. Significant differences were calculated for the theront mortality data by analysis of variance followed by Dunnet's posthoc analyses (p<0.05). Results The viscosin, massetolide and putisolvin biosurfactants extract from *Pseudomonas* sp H6, *Pseudomonas fluorescens* SS101 and *Pseudomonas putida* 267, respectively, elicited 100% mortality of theronts during the first 5 min exposure at a concentration 0.15 mg/mL. At a concentration of 0.015 mg/ml, massetolide and viscosin-like biosurfactant elicited 90% and 50% mortality of theronts within 15 min, whereas putisolvin had no effect at this concentration (FIG. 3).

Tomonts were killed at 0.1 mg/ml within 15 minutes upon exposure of the viscosin-like biosurfactant of *Pseudomonas* H6. Tomonts exposed to 1.5 and 0.15 mg/mL of massetolide were lethal within 15 min of exposure, whereas putisolvin killed tomonts at 1.5 mg/mL within the first 15 min, but no effects were observed at a concentration 0.15 mg/mL (Table 1).

TABLE 1

Effect of biosurfactants on number of tomonts. The biosurfactants included were massetolide obtained from *Pseudomonas fluorescens* SS101, the putisolvin-like biosurfactant from *Pseudomonas putida* 267.

| | | number of tomonts | | |
|---|---|---|---|---|
| concentration | time | water control | massetolide | putisolvin |
| 1.5 mg/ml | 0 min | 2 | 2 | 2 |
| | 15 min | 2 | 0 | 0 |
| | 30 min | 2 | 0 | 0 |
| | 45 min | 2 | 0 | 0 |
| | 60 min | 2 | 0 | 0 |
| 0.15 mg/ml | 0 min | 2 | 2 | 2 |
| | 15 min | 2 | 0 | 2 |
| | 30 min | 2 | 0 | 2 |
| | 45 min | 2 | 0 | 2 |
| | 60 min | 2 | 0 | 2 |

CONCLUSIONS

The viscosin-like biosurfactant of *Pseudomonas* H6 showed clear inhibitory effect on the free-living tomont and theront life stages of Ich at concentrations 100 and 10-20 ug/ml, respectively.

Structurally related biosurfactant massetolide (produced by *Pseudomonas fluorescens* SS101) showed similar activity as the viscosin-like biosurfactant from *Pseudomonas* H6 towards theronts and tomonts. Putisolvin, which is structurally more distant from the visocosin-like biosurfactant of H6, is less active at lower concentrations against theronts and not active against tomonts.

REFERENCES de Bruijn et al. (2007): de Bruijn I, de Kock M J D, Yang M, de Waard P, van Beek T A, Raaijmakers J M. "Genome-based discovery, structure prediction and functional analysis of cyclic lipopeptide antibiotics in *Pseudomonas* species." Molecular Microbiology. 2007; 63 (2): 417-28.
De Bruijn et al (2008): De Bruijn I, De Kock M J D, De Waard P, Van Beek T A, Raaijmakers J M. "Massetolide A Biosynthesis in *Pseudomonas fluorescens*." *J Bacteriol* 190, 2777-2789 (2008).
Liu et al. (2015): Yiying Liu, Elzbieta Rzeszutek, Menno van der Voort, Cheng-Hsuan Wu, Even Thoen, Ida Skaar, Vincent Bulone, Pieter C. Dorrestein, Jos M. Raaijmakers, Irene de Bruijn "Diversity of Aquatic *Pseudomonas* Species and Their Activity against the Fish Pathogenic Oomycete *Saprolegnia*" PLOSOne; DOI: 10.1371/journal.pone.0136241; published 28. August 2016.
Xueqin et al. (2012): Xueqin J, Kania μW and Buchmann K. "Comparative effects of four feed types on white spot disease susceptibility and skin immune parameters in rainbow trout, *Oncorhynchus mykiss* (Walbaum)" J Fish Dis. 2012 February; 35 (2): 127-35.
Aihua, L., Buchmann, K. (2001). "Temperature- and salinity-dependent development of a Nordic strain of *Ichthyophthirius multifiliis* from rainbow trout." J Appl Ichthyol 17, 273-276.
Kruijt et al (2008): Kruijt M, Tran H, Raaijmakers J M. "Functional, genetic and chemical characterization of biosurfactants produced by plant growth-promoting *Pseudomonas putida* 267." *Journal of applied microbiology* 107, 546-556 (2009).

The invention claimed is:

1. A method for treating white spot disease in fish using a lipopeptide biosurfactant.

2. A method according to claim 1, wherein the lipopeptide biosurfactant is selected from a viscosin lipopeptide or a derivative thereof.

3. A method according to claim 2, wherein the viscosin lipopeptide is a viscosin-like lipopeptide obtainable from the *Pseudomonas fluorescens* strain H6.

4. A method according to claim 1, wherein the lipopeptide biosurfactant is selected from a massetolide lipopeptide or a derivative thereof.

5. A method according to claim 1, wherein the massetolide lipopeptide a massetolide surfactant obtainable from the *Pseudomonas fluorescens* strain SS101.

6. A method according to claim 1, wherein the lipopeptide biosurfactant is selected from a putisolvin lipopeptide or a derivative thereof.

7. A method according to claim 6, wherein the putisolvin lipopeptide is a putisolvin biosurfactant obtainable from *Pseudomonas putida* 267.

8. A method according to claim 1, wherein the method is for treating an *Ichthyophthirius multifiliis* infection.

9. A method according to claim 1, wherein the method comprises administering the lipopeptide biosurfactant to the fish.

10. A method according to claim 9, wherein the method comprises administering the lipopeptide biosurfactant as a bacterial culture, wherein the bacterial culture produces the lipopeptide biosurfactant.

11. A method according to claim 10, wherein the bacterial culture comprises *Pseudomonas fluorescens* strain H6.

12. A method according to claim 1, wherein the method comprises administering the lipopeptide biosurfactant to fish tank water in a concentration of 10-1000 μg/ml.

13. A method according to claim 1, wherein the method comprises performing the treatment several times.

14. A method according to claim 1, wherein the method comprises treating white spot disease in fish using a composition, wherein the composition comprises the lipopeptide biosurfactant.

15. A method according to claim 14, wherein the lipopeptide biosurfactant is a lipopeptide obtainable from a *Pseudomonas* species.

16. A method according to claim 15, wherein the lipopeptide is obtainable from *Pseudomonas fluorescens* strain H6.

17. A method according to claim 14, wherein the composition comprises the lipopeptide biosurfactant in a concentration of 10-1000 μg/ml.

18. A method according to claim 14, wherein the composition comprises one or more carriers, and wherein the composition comprises a slow-release form which sheds the lipopeptide biosurfactant over a prolonged period.

19. A method according to claim 1, further comprising preparing the composition comprising the lipopeptide biosurfactant, wherein the preparation comprises acidic precipitation of the lipopeptide biosurfactant.

20. A method according to claim 19, further comprising redissolution and drying of the precipitate.

* * * * *